United States Patent
Kabot

(10) Patent No.: US 11,351,373 B2
(45) Date of Patent: Jun. 7, 2022

(54) MONOPHASIC STIMULATION PULSES WITH ALTERNATING POLARITY AND EXTRAORDINARY POLARITY CHANGES

(71) Applicant: MED-EL Elektromedizinische Geraete GmbH, Innsbruck (AT)

(72) Inventor: Ernst Kabot, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 16/756,385

(22) PCT Filed: Nov. 12, 2018

(86) PCT No.: PCT/US2018/060258
§ 371 (c)(1),
(2) Date: Apr. 15, 2020

(87) PCT Pub. No.: WO2019/094855
PCT Pub. Date: May 16, 2019

(65) Prior Publication Data
US 2020/0276443 A1  Sep. 3, 2020

Related U.S. Application Data

(60) Provisional application No. 62/585,104, filed on Nov. 13, 2017.

(51) Int. Cl.
*A61N 1/36* (2006.01)
*A61N 1/04* (2006.01)
(Continued)

(52) U.S. Cl.
CPC ....... *A61N 1/36038* (2017.08); *A61N 1/0476* (2013.01); *A61N 1/0541* (2013.01); *A61N 1/36175* (2013.01); *G10L 25/48* (2013.01)

(58) Field of Classification Search
None
See application file for complete search history.

(56) References Cited

U.S. PATENT DOCUMENTS 4,495,384 A  1/1985 Scott et al.
9,937,344 B2 *  4/2018 Starkebaum ....... A61N 1/36007
(Continued)

OTHER PUBLICATIONS

International Searching Authority/US, International Search Report and Written Opinion of the International Searching Authority, Application No. PCT/US2018/060258, dated Jan. 16, 2019, 14 pages.

*Primary Examiner* — Erica S Lee
(74) *Attorney, Agent, or Firm* — Sunstein LLP

(57) ABSTRACT

Arrangements are described for generating electrode stimulation signals to electrode contacts in an implanted cochlear implant electrode array. Electrode stimulation signals are a sequence of monophasic stimulation pulses varying in polarity between positive polarity and negative polarity with successive pulses separated in time by an interpulse interval sufficient for neural response. Accumulated charge imbalance and charge imbalance polarity are calculated for each electrode contact after each stimulation pulse. For each electrode contact a stimulation pulse has the same polarity as an immediately preceding stimulation pulse for that electrode contact only when the charge imbalance polarity has opposite polarity from the immediately preceding stimulation pulse for that electrode contact, and the accumulated charge imbalance exceeds a defined charge imbalance threshold value. Otherwise, each stimulation pulse has the opposite polarity as the immediately preceding stimulation pulse for that electrode contact.

20 Claims, 10 Drawing Sheets

(51) Int. Cl.
  *A61N 1/05*      (2006.01)
  *G10L 25/48*     (2013.01)

(56) References Cited

U.S. PATENT DOCUMENTS

2001/0047193 A1     11/2001   Zierhofer et al.
2016/0144179 A1      5/2016   Fridman et al.
2017/0113041 A1*     4/2017   Karunasiri ............ A61N 1/0541
2018/0369593 A1*    12/2018   Johanek ............. A61N 1/36171

* cited by examiner

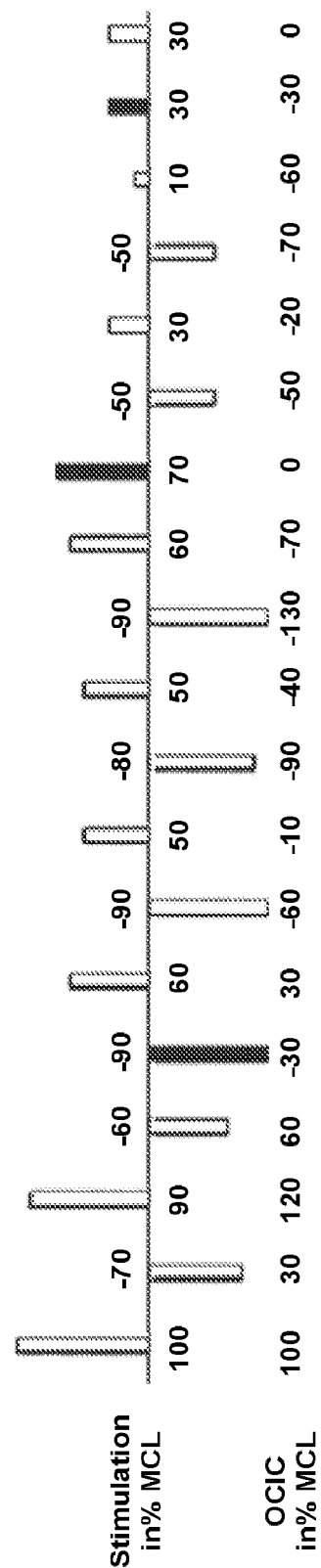

MONOPHASIC STIMULATION PULSES WITH ALTERNATING POLARITY AND EXTRAORDINARY POLARITY CHANGES

This application claims priority from U.S. Provisional Patent Application 62/585,104, filed Nov. 13, 2017, which is incorporated herein by reference in its entirety.

TECHNICAL FIELD

The present invention relates to signal processing arrangements for hearing implants, and more particularly, to speech coding strategies for cochlear implants.

BACKGROUND ART

As shown in FIG. 1, sounds are transmitted by a human ear from the outer ear 101 to the tympanic membrane (eardrum) 102, which moves the bones of the middle ear 103 (malleus, incus, and stapes) that vibrate the oval window and round window openings of the cochlea 104. The cochlea 104 is a long fluid-filled duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the cochlea 104 functions as a transducer to generate electric pulses which are transmitted to the cochlear nerve 113, and ultimately to the brain which perceives the neural signals as sound.

Hearing is impaired when there are problems in the ability to transduce external sounds into meaningful action potentials along the neural substrate of the cochlea 104. To improve impaired hearing, hearing prostheses have been developed. In some cases, hearing impairment can be addressed by a cochlear implant (CI), a brainstem-, midbrain- or cortical implant that electrically stimulates auditory neural tissue with small currents delivered by multiple electrode contacts distributed along an implant electrode. For cochlear implants, the electrode array is inserted into the cochlea 104. For brain-stem, midbrain and cortical implants, the electrode array is located in the auditory brainstem, midbrain or cortex, respectively.

FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing, spectral peak (SPEAK) digital signal processing, fine structure processing (FSP) and compressed analog (CA) signal processing. The processed signal is converted by the external signal processor 111 into a digital data format, such as a sequence of data frames, for transmission by an external coil 107 into a receiving stimulation processor 108. Besides extracting the audio information, the receiver processor in the stimulation processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple electrode contacts 112 on its surface that provide selective electrical stimulation of the cochlea 104.

FIG. 2 shows an example of an electrode contact configuration used in a 12-channel electrode array as described in U.S. Pat. No. 6,600,955. An electrode array containing 12 electrode contacts 201 (black dots) is positioned within the scala tympani of the cochlea. Each of these electrode contacts 201 is connected to a capacitor C 203 and a pair of current sources 205 and 207, whereby the second ports of current sources 205 and 207 are connected to implant ground GND 209 and implant supply voltage $V_{CC}$ 211, respectively. Current sources 205 and 207 may be implemented, for example, using P-channel and N-channel MOS field effect transistors, respectively. Thus, for convenience, the current sources 205 and 207 are designated as P-sources and N-sources. Reference electrode 213 is positioned outside the cochlea and connected to a pair of switches 215 and 217, whereby the second ports of switches 215 and 217 are connected to implant ground GND and implant supply voltage $V_{CC}$, respectively.

An audio signal, such as speech or music, can be processed into multiple frequency band pass signals, each having a signal envelope and fine time structure within the envelope. One common speech coding strategy is the so called "continuous-interleaved-sampling strategy" (CIS), as described by Wilson B. S., Finley C. C., Lawson D. T., Wolford R. D., Eddington D. K., Rabinowitz W. M., "Better speech recognition with cochlear implants," Nature, vol. 352, 236-238 (July 1991), which is hereby incorporated herein by reference. The CIS speech coding strategy samples the signal envelopes at predetermined time intervals, and derives the amplitude of the stimulation pulses from the envelopes of the bandpass signals, providing a remarkable level of speech understanding merely by coding the signal envelope of the speech signal. This can be explained, in part, by the fact that auditory neurons phase lock to amplitude modulated electrical pulse trains (see, for example, Middlebrooks, J. C., "Auditory Cortex Phase Locking to Amplitude-Modulated Cochlear Implant Pulse Trains," J Neurophysiol, 100(1), p. 76-912008, 2008 July, which is hereby incorporated herein by reference). However, for normal hearing subjects, both signal cues, the envelope and the final time structure, are important for localization and speech understanding in noise and reverberant conditions (Zeng, Fan-Gang, et al. "Auditory perception with slowly-varying amplitude and frequency modulations." *Auditory Signal Processing*, Springer New York, 2005, 282-290; Drennan, Ward R., et al. "Effects of temporal fine structure on the lateralization of speech and on speech understanding in noise." *Journal of the Association for Research in Otolaryngology* 8.3 (2007): 373-383; and Hopkins, Kathryn, and Brian Moore. "The contribution of temporal fine structure information to the intelligibility of speech in noise," *The Journal of the Acoustical Society of America* 123.5 (2008): 3710-3710; and all of which are hereby incorporated herein by reference in their entireties).

Older speech coding strategies mainly encode the slowly varying band pass envelope information and do not transmit the fine time structure of the band pass signal. Some more recent coding strategies, for example, Fine Structure Processing (FSP), do also transmit the fine time structure information. In FSP, the fine time structure of low frequency channels is transmitted through Channel Specific Sampling Sequences (CSSS) that start at negative to positive zero crossings of the respective band pass filter output (see U.S. Pat. No. 6,594,525, which is incorporated herein by reference). The basic idea of FSP is to apply a stimulation pattern, where a particular relationship to the center frequencies of the filter channels is preserved, i.e., the center frequencies are represented in the temporal waveforms of the stimulation patterns, and are not fully removed, as is done in CIS. Each stimulation channel is associated with a particular CSSS, which is a sequence of ultra-high-rate biphasic pulses (typically 5-10 kpps). Each CSSS has a distinct length (number of pulses) and distinct amplitude distribution. The amplitude of the maximum pulse within each CSSS is equal to the maximum of the associated half-wave-pulse of the band pass filter. The length of a CSSS may be derived, for example, from the center frequency of the associated band pass filter. A CSSS associated with a lower filter channel is longer than a CSSS associated with a higher filter channel. For example, it may be one half of the period of the center frequency. The amplitude distribution may be adjusted to patient specific requirements.

FIGS. 3A-3B show two examples of CSSS for a 6-channel system. In FIG. 3A, the CSSS's are derived by sampling one half of a period of a sinusoid whose frequency is equal to the center frequency of the band pass filter (center frequencies at 440 Hz, 696 Hz, 1103 Hz, 1745 Hz, 2762 Hz, and 4372 Hz). Sampling is achieved by means of biphasic pulses at a rate of 10 kpps and a phase duration of 25 µs. For Channels 5 and 6, one half of a period of the center frequencies is too short to give space for more than one stimulation pulse, i.e., the "sequences" consist of only one pulse, respectively. Other amplitude distributions may be utilized. For example, in FIG. 3B, the sequences are derived by sampling one quarter of a sinusoid with a frequency, which is half the center frequency of the band pass filters. These CSSS's have about the same durations as the CSSS's in FIG. 3A, respectively, but the amplitude distribution is monotonically increasing. Such monotonic distributions might be advantageous, because each pulse of the sequence can theoretically stimulate neurons at sites which cannot be reached by its predecessors.

FIG. 4 illustrates a typical signal processing implementation of the FSP coding strategy. A Filter Bank 401 processes an audio input signal to generate band pass signals that each represent a band pass channel defined by an associated band of audio frequencies. The output of the Filter Bank 401 goes to a Stimulation Signal Processor 400 that includes an Envelope Detector 402 that extracts band pass envelope signals reflecting time varying amplitude of the band pass signals which includes unresolved harmonics and are modulated with the difference tones of the harmonics, mainly the fundamental frequency F0, and to a Stimulation Timing Module 403 that generates stimulation timing signals reflecting the temporal fine structure features of the band pass signals. For FSP, the Stimulation Timing Module 403 detects the negative to positive zero crossings of each band pass signal and in response starts a CSSS as a stimulation timing signal. The Stimulation Signal Processor 400 also includes a Pulse Generator 404 uses the band pass envelope signals and the stimulation timing signals to produce the electrode stimulation signals for the electrode contacts in the implant 405.

FSP and FS4 are the sole commercially available coding strategies that code the temporal fine structure information. Although they have be shown to perform significantly better than e.g. CIS in many hearing situations, there are some other hearing situations in which no significant benefit has been found so far over CIS-like envelope-only coding strategies, in particular with regard to localization and speech understanding in noisy and reverberant conditions.

SUMMARY

Embodiments of the present invention are directed to systems and methods for generating electrode stimulation signals for the electrode contacts in a cochlear implant electrode array. A band pass filter bank is configured for processing an audio input signal to generate multiple band pass signals each representing an associated band of audio frequencies in the audio input signal. A stimulation signal processor is configured for generating electrode stimulation signals for the electrode contacts based on the band pass signals. For each electrode contact, the electrode stimulation signal is a sequence of monophasic stimulation pulses varying in polarity between positive polarity and negative polarity with successive pulses separated in time by an interpulse interval sufficient for neural response. A charge imbalance module is configured for calculating accumulated charge imbalance and charge imbalance polarity for each electrode contact after each stimulation pulse. For each electrode contact, a stimulation pulse has the same polarity as an immediately preceding stimulation pulse for that electrode contact only when the charge imbalance polarity has opposite polarity from the immediately preceding stimulation pulse for that electrode contact, and the accumulated charge imbalance exceeds a defined charge imbalance threshold value. Otherwise, each stimulation pulse has the opposite polarity as the immediately preceding stimulation pulse for that electrode contact.

In further specific embodiments, the charge imbalance module may be configured for calculating the accumulated charge imbalance in terms of maximum comfortable level (MCL) for each electrode contact and/or the defined charge imbalance threshold value may be defined in terms of maximum comfortable level (MCL) for each electrode contact. Each sequence of monophasic stimulation pulses may end with a final charge balancing stimulation pulse having a polarity and amplitude offsetting the accumulated charge imbalance and charge imbalance polarity so that after the final charge balancing stimulation pulse the accumulated charge imbalance is zero.

The stimulation pulses may have a constant or variable pulse width. And the interpulse interval may be a fixed time duration or a variable time duration. The charge imbalance module may be located in an implanted stimulation processor implanted under the skin of a patient user, or in an external signal processor attached to the skin of a patient user.

BRIEF DESCRIPTION OF THE DRAWINGS

FIG. 10 shows an example of a stimulation pulse sequence according to an embodiment of the present invention.

DETAILED DESCRIPTION

Cochlear implants typically apply charge-balanced biphasic or charge-balanced triphasic stimulation pulses for electrical stimulation. It has been shown that anodic-first and cathodic-first pulses result in different loudness percepts, probably related to individual neural survival status. Also charge-balanced pseudo-monophasic pulses (first phase high amplitude and short duration, second phase low amplitude and long duration) have been used in research where lower MCLs have been observed for anodic-first pulse shapes. Lowest MCL thresholds have been found for alternating monophasic waveforms where two succeeding monophasic pulses of alternating polarity and same absolute amplitude were applied with 5 ms inter-pulse gap (sufficient for neural response). But charge balancing is required for safety reasons so pure monophasic stimulation with independent amplitudes has not been considered usable in humans. But embodiments of the present invention introduce a novel and inventive form of monophasic stimulation that is charge balanced over time. This is also the most efficient waveform for stimulation so considerably lower energy is used for stimulation without restrictions in perception.

Figure 1:
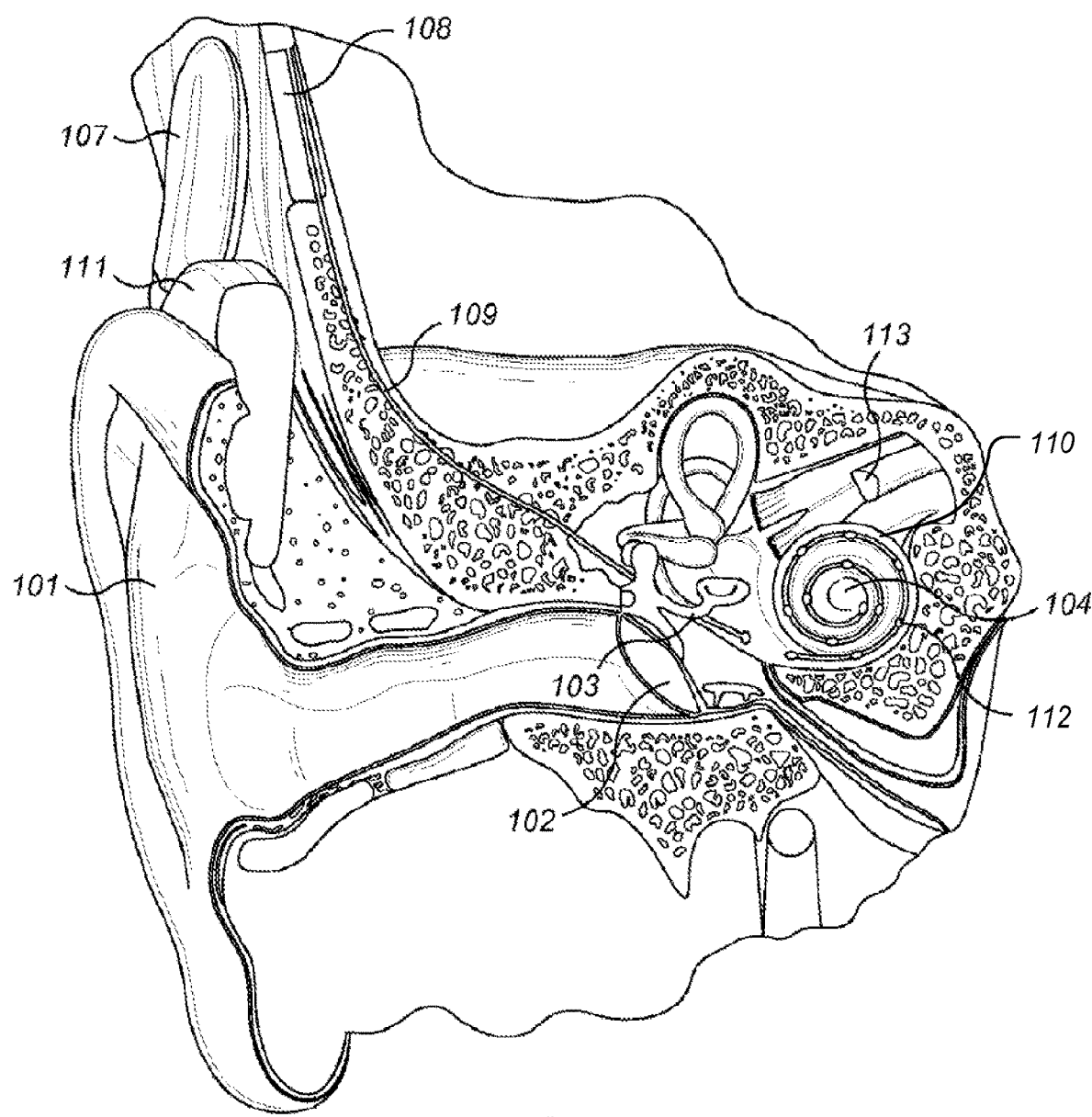
FIG. 1 shows anatomical structures of a human ear and some components of a typical cochlear implant system.
Figure 2:
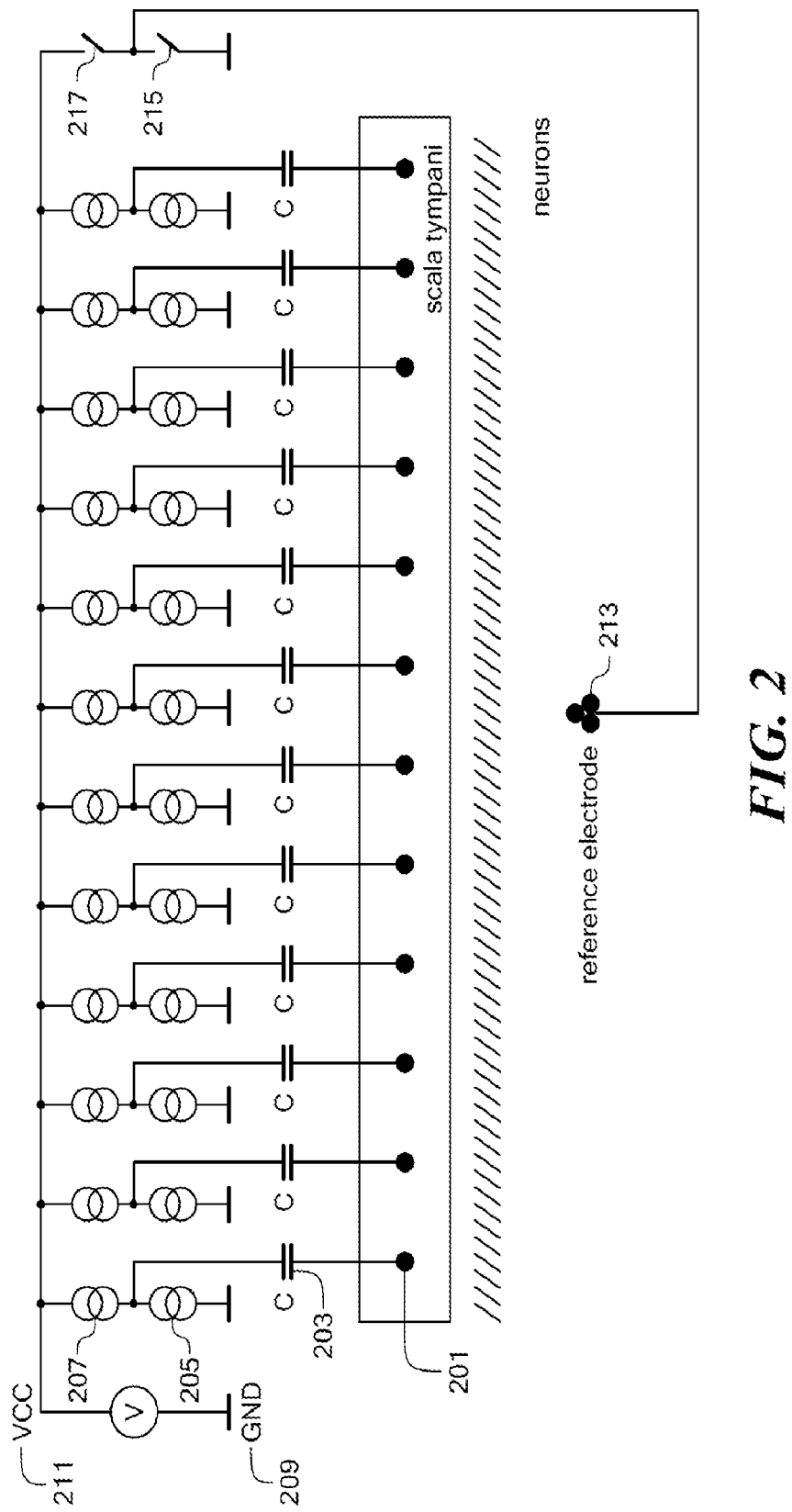
FIG. 2 shows an example of an electrode contact configuration used in a 12-channel electrode array
Figure 3A:
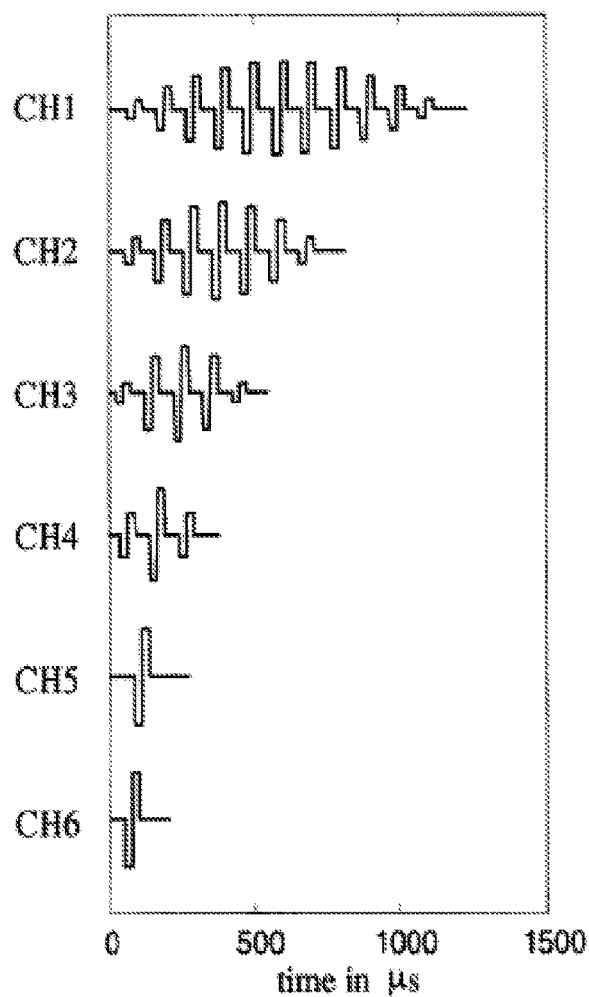
FIG. 3A shows channel specific sampling sequences (CSSS) for two 6-channel systems utilizing biphasic pulses at 10 kpps and phase duration of 25 µs derived from a sinusoid within [0–π].
Figure 3B:
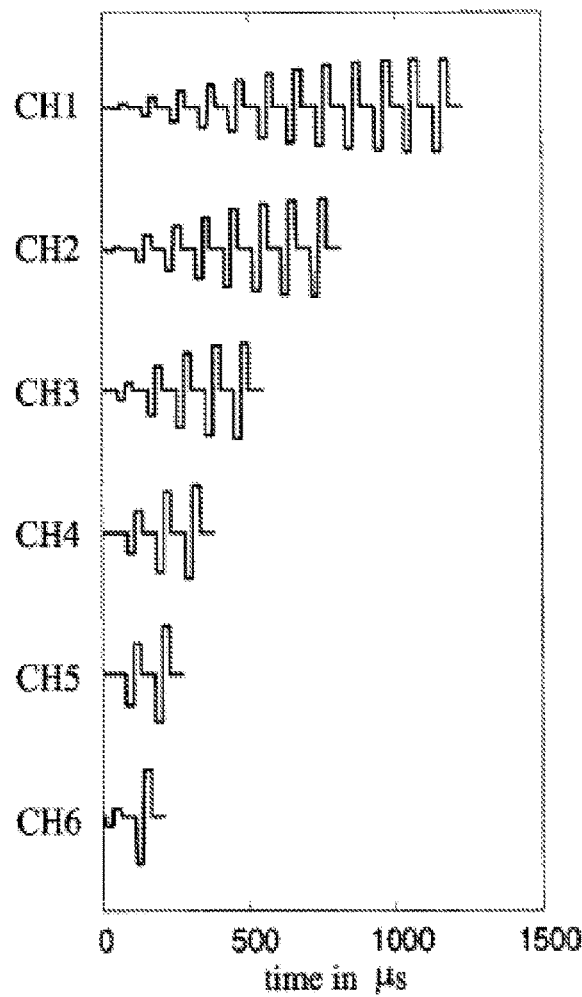
FIG. 3B shows channel specific sampling sequences (CSSS) for two 6-channel systems utilizing biphasic pulses at 10 kpps and phase duration of 25 µs derived from a sinusoid within [0–π/2], amplitudes monotonically increasing.
Figure 4:
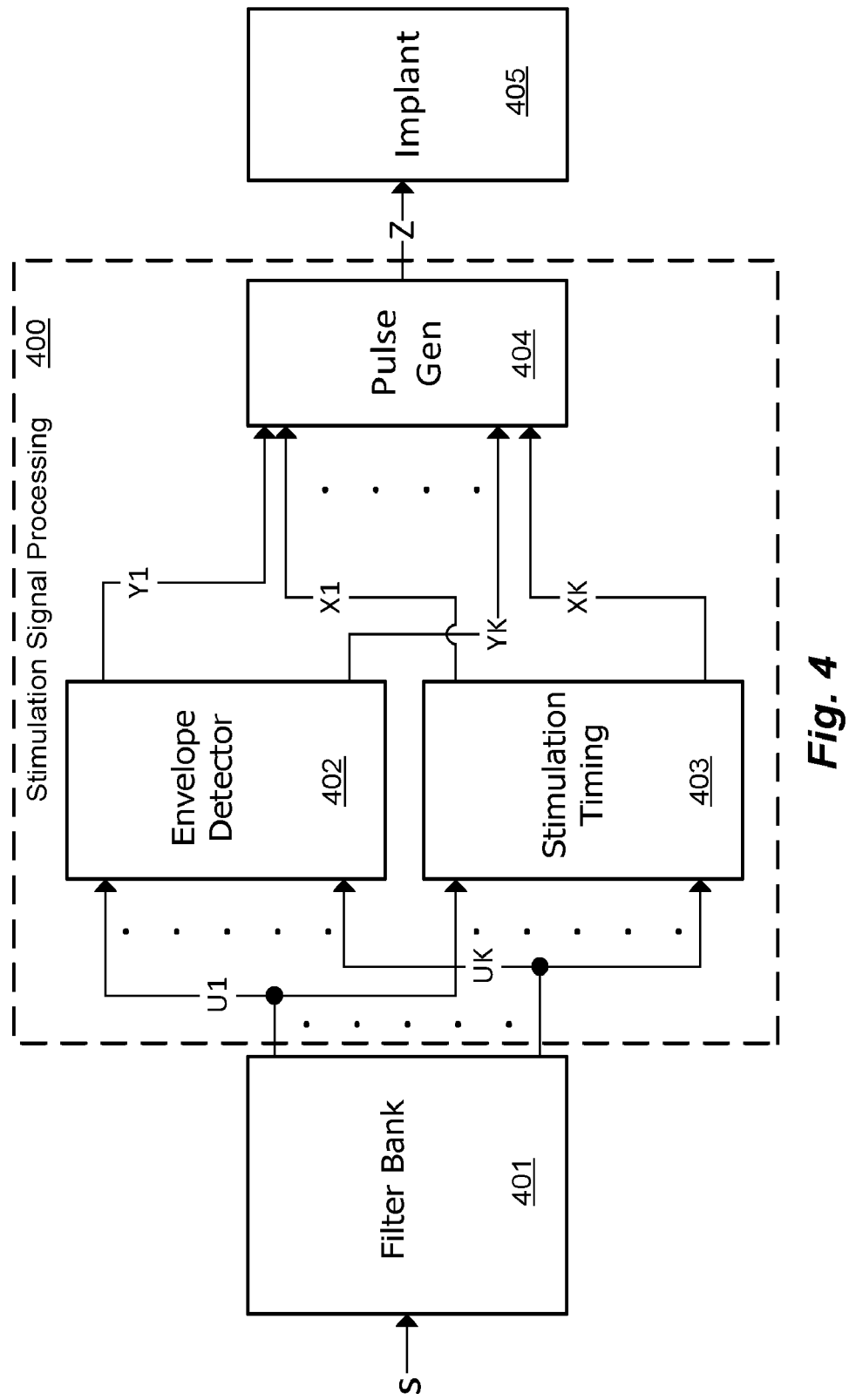
FIG. 4 shows various functional blocks in a signal processing arrangement for a hearing implant.
Figure 5:
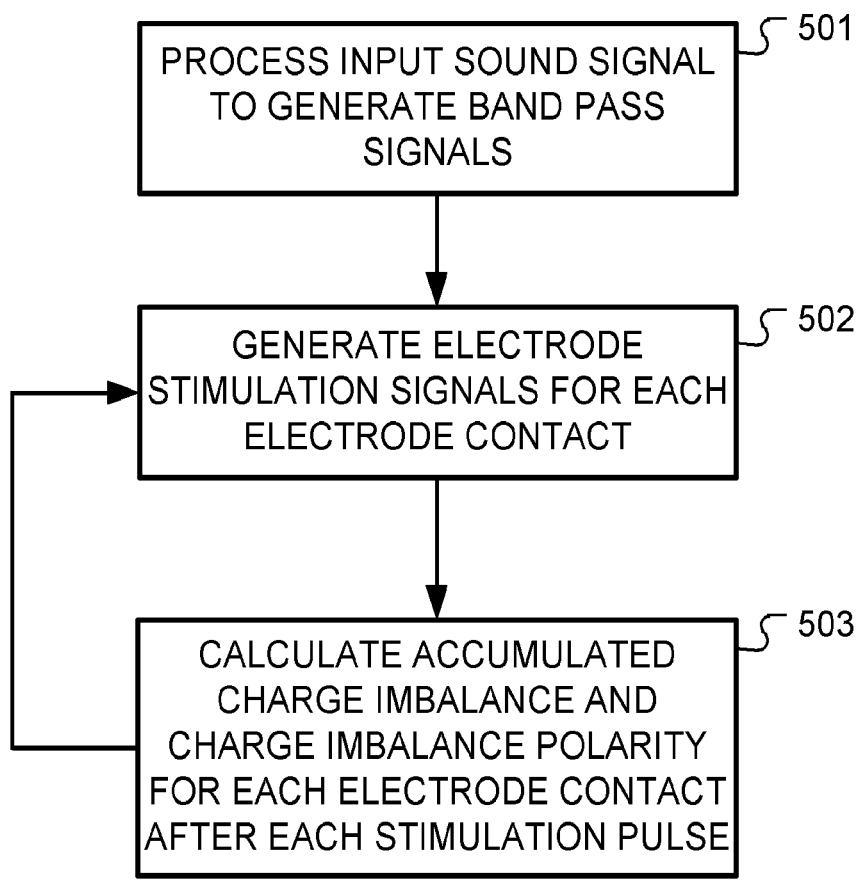
FIG. 5 shows various logical steps in developing electrode stimulation signals according to an embodiment of the present invention.
Figure 6:
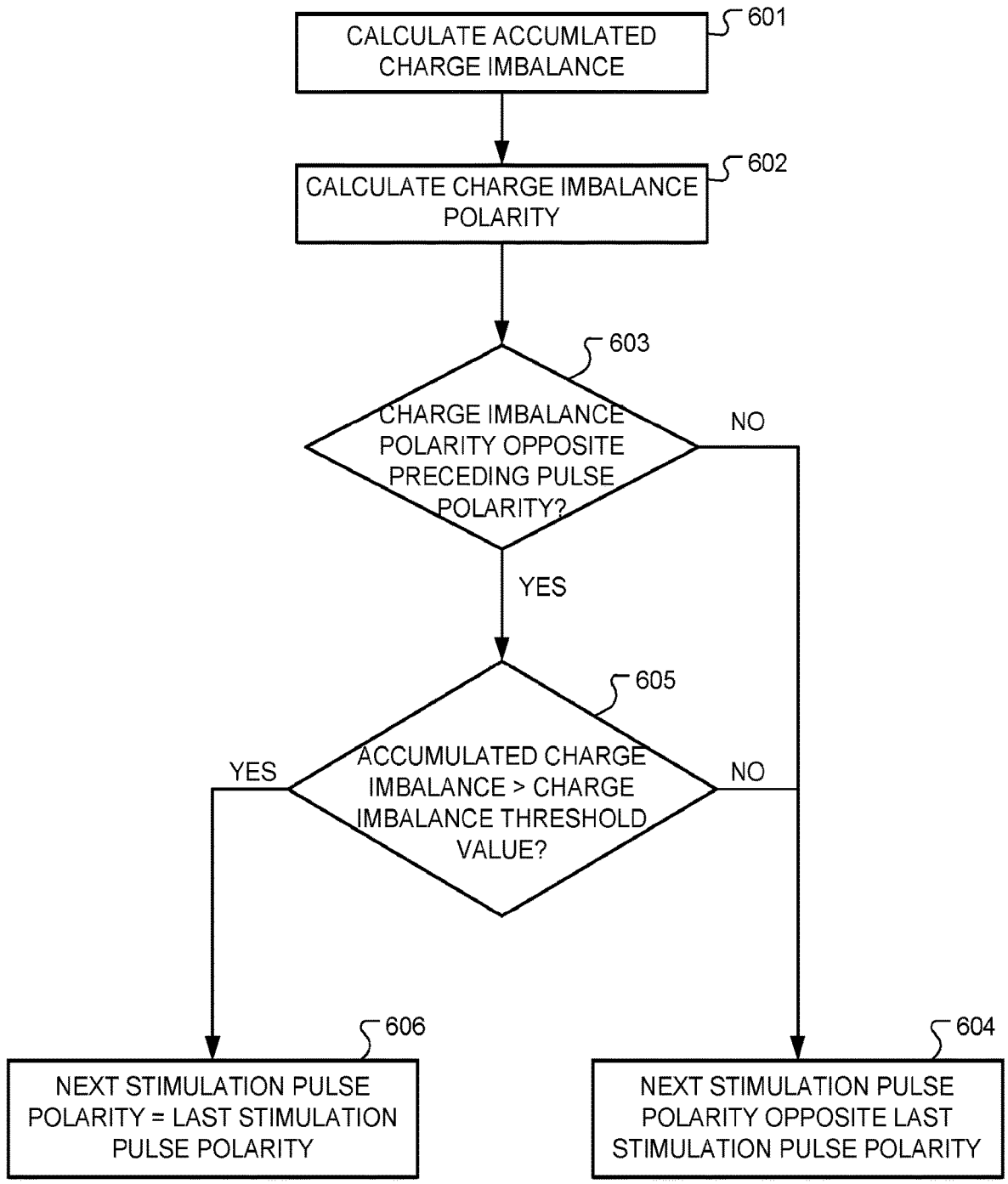
FIG. 6 shows greater detail as to logical steps in developing electrode stimulation signals according to an embodiment of the present invention.
Figure 7:
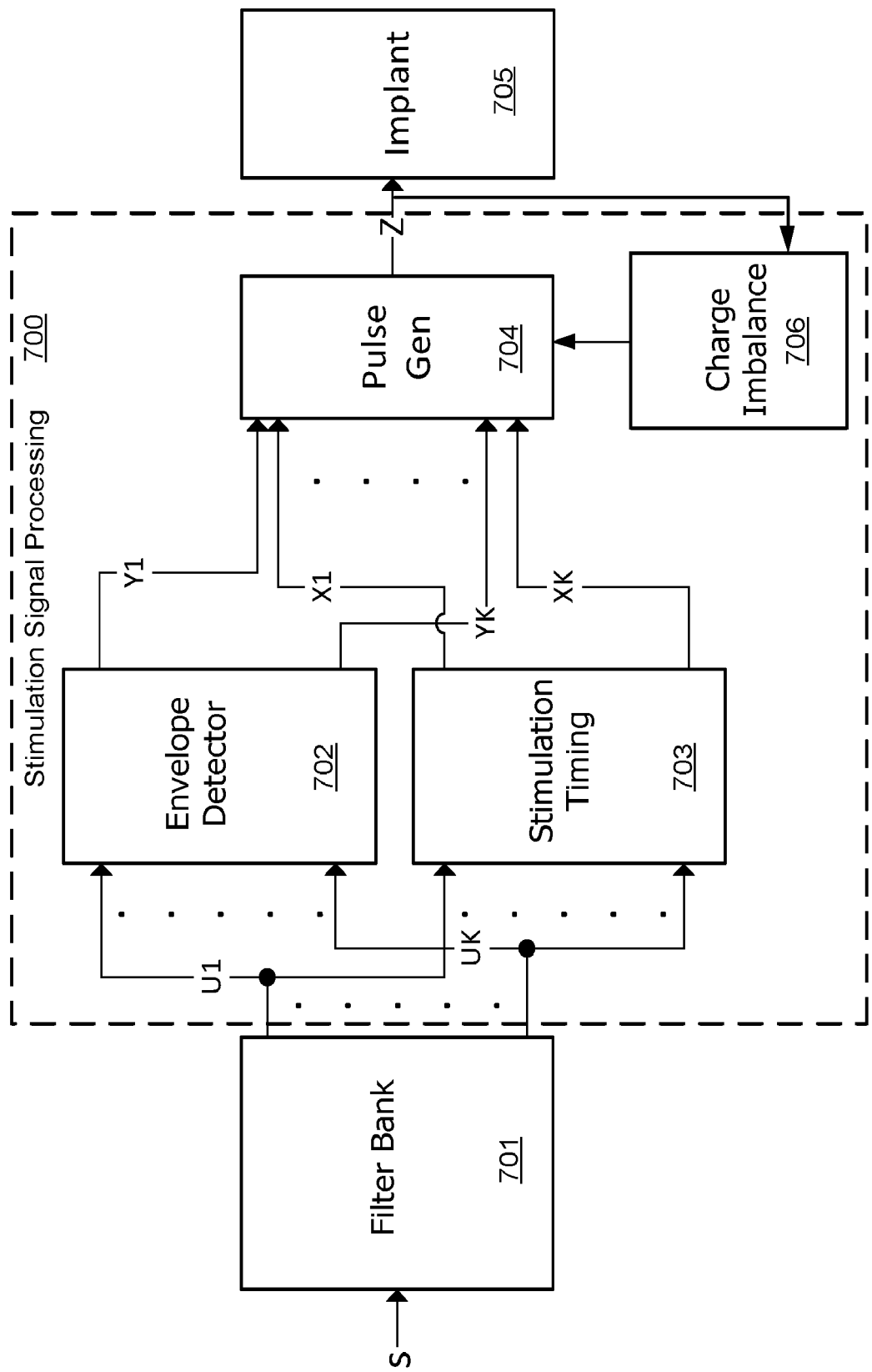
FIG. 7 shows various functional blocks in a signal processing arrangement for a hearing implant according to an embodiment of the present invention.

FIGS. 5 and 6 are flow charts showing various logical steps and FIG. 7 shows various functional blocks in a signal processing arrangement for a cochlear implant that produces electrode stimulation signals to electrode contacts in an implanted cochlear implant array according to an embodiment of the present invention. A pseudo code example of such a method can be set forth as:
Band Pass Processing:
  BandPassFilter (input_sound, bp_signals)
Accumulated Charge Imbalance:
  ChargeImbalance (stim_signals, accum_charge_imbalance, charge_imbalance_polarity)
Pulse Generation:
  PulseGenerate (bp_signals, accum_charge_imbalance, charge_imbalance_polarity, stim_signals)
The details of such an arrangement are set forth in the following discussion.

In the arrangement shown in FIG. 7, the audio input signal is produced by one or more sensing microphones, which may be omnidirectional and/or directional. Filter Bank 701 processes the audio input signal, step 501, with a bank of multiple parallel band pass filters, each of which is associated with a specific band of audio frequencies; for example, using a filter bank with 12 digital Butterworth band pass filters of 6th order, Infinite Impulse Response (IIR) type, so that the audio input signal is filtered into some K band pass signals, $U_1$ to $U_K$ where each signal corresponds to the band of frequencies for one of the band pass filters. Each output of the Filter Bank 701 can roughly be regarded as a sinusoid at the center frequency of the band pass filter which is modulated by an amplitude envelope signal. This is due to the quality factor ($Q \approx 3$) of the filters. In case of a voiced speech segment, the band pass envelope is approximately periodic, and the repetition rate is equal to the pitch frequency. Alternatively and without limitation, the Filter Bank 701 may be implemented based on use of a fast Fourier transform (FFT) or a short-time Fourier transform (STFT). Based on the tonotopic organization of the cochlea, each electrode contact in the scala tympani typically is associated with a specific band pass channel of the Filter Bank 701. The Band Pass Filter Bank 701 also may perform other initial signal processing functions such as automatic gain control (AGC) and/or noise reduction.

Figure 8:
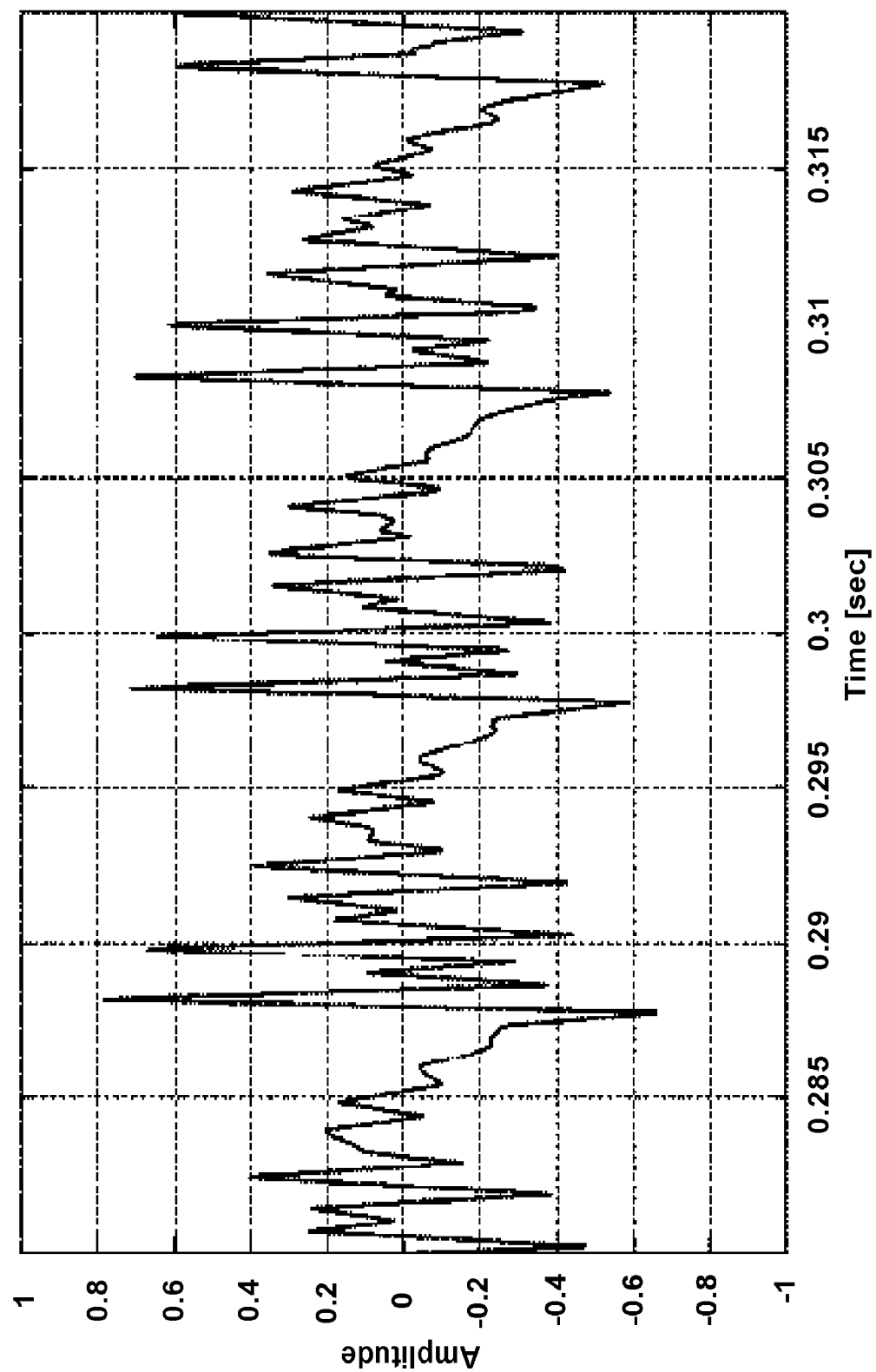
FIG. 8 shows an example of a short time period of an input speech signal from a sensing microphone.
Figure 9:
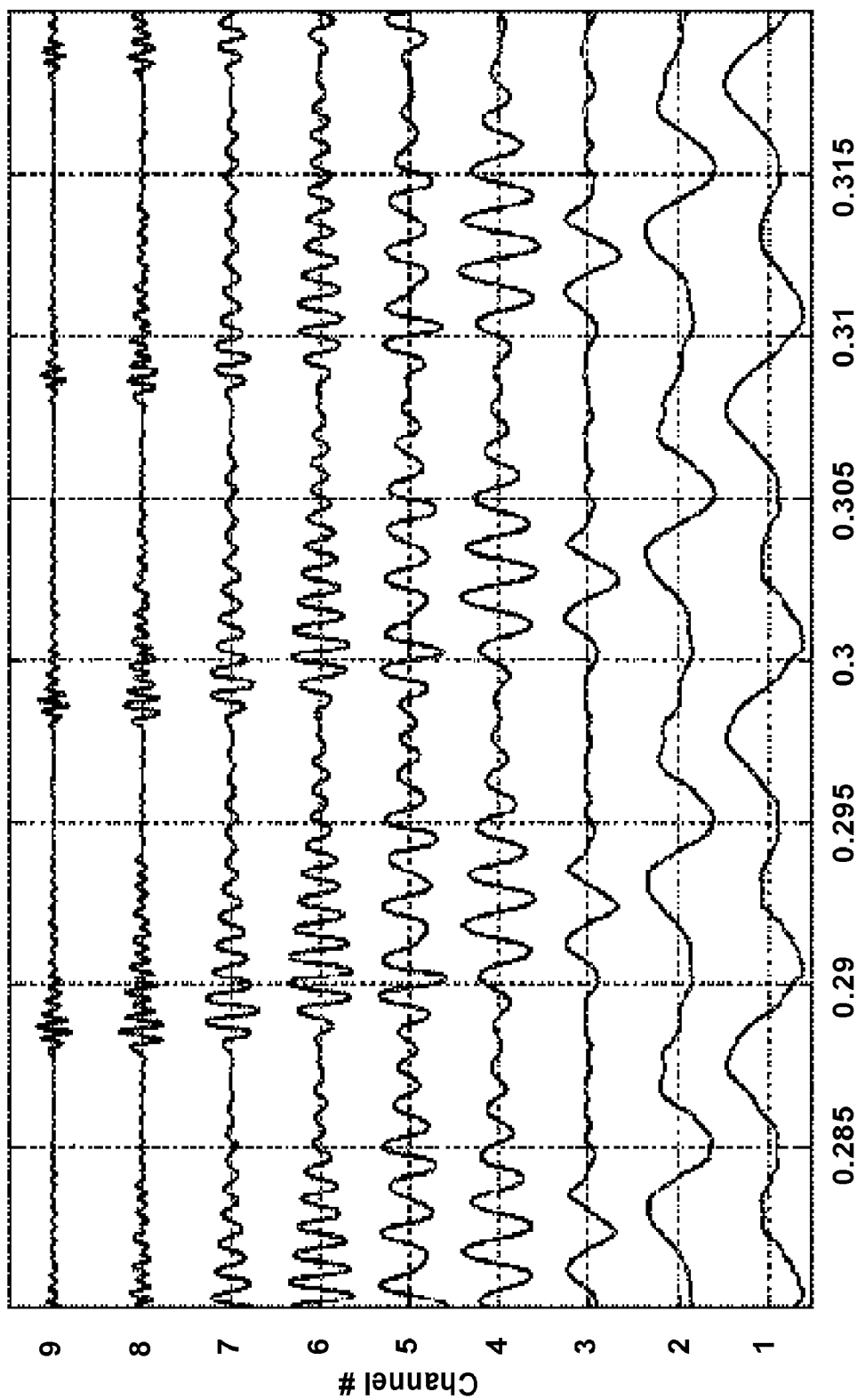
FIG. 9 shows the microphone signal decomposed by band-pass filtering by a bank of filters.

FIG. 8 shows an example of a short time period of an audio input signal from a sensing microphone, and FIG. 9 shows the microphone signal decomposed by band-pass filtering by a bank of filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety:

```
for j = 0 to number of channels − 1 do
    for s = 0 to number of samples − 1 do
        Y_j(s) = B_{0j} *X_j(s) + Z_{0j}
        for i = 0 to order− 3 do
            Z_{ij} = B_{i+1, j} *X_j(s) + Z_{i+1,j} − A_{i+1, j} * Y_j(s)
        end for
        Z_{order−2,j} = B_{order− 1, j} * X_j(s) −A_{order−1,j} * Y_j(s)
    end for
end for
```

The band pass signals $U_1$ to $U_K$ (which can also be thought of as electrode channels) are output to a Stimulation Signal Processor 700 that generates the electrode stimulation signals for each electrode contact, step 502. Specifically, the Stimulation Signal Processor 700 includes an Envelope Detector 702 which extracts characteristic band pass envelope signals outputs $Y_1, \ldots, Y_K$ that represent the channel-specific time varying amplitudes of the band pass signals $U_1$ to $U_K$. The envelope extraction can be represented by $Y_k = LP(|U_k|)$, where |.| denotes the absolute value and LP(.) is a low-pass filter; for example, using 12 rectifiers and 12 digital Butterworth low pass filters of 2nd order, IIR-type. A properly selected low-pass filter can advantageously smooth the extracted envelope to remove undesirable fluctuations. Alternatively, if the band pass signals $U_1, \ldots, U_K$ are generated by orthogonal filters, the Envelope Detector 702 may extract the Hilbert envelope. In some embodiments, the Envelope Detector 702 may also be configured to determine one or more other useful features of the band pass envelope such as envelope slope (e.g., based on the first derivative over time of the envelope), envelope peak (ascending slope/positive first derivative followed by descending slope/negative first derivative), and/or envelope amplitude of the band pass envelope.

A Stimulation Timing Module 703 in the Stimulation Signal Processor 700 processes the band pass signals on a regular time grid (e.g. 1000 pps) based on selected temporal fine structure features such as negative-to-positive zero crossings to generate band pass timing pulses. In some embodiments, the Stimulation Timing Module 703 may limit the instantaneous band pass frequency $f_0$ to the upper and lower frequency boundaries $f_{L1}$ and $f_{U1}$ of the respective filter band. For example, a given band pass signal may have a lower frequency boundary $f_{L1}$ of 700 Hz and an upper frequency boundaries of $f_{U1}$=770 Hz.

The Stimulation Signal Processor 700 also includes a Pulse Generation Module 704 that generates the electrode stimulation signals for the electrode contacts in the Implant 705 by generating one or more corresponding stimulation pulses for each band pass signal. For each electrode contact, the electrode stimulation signal is a sequence of monophasic stimulation pulses that vary in polarity between positive polarity and negative polarity with successive pulses separated in time by an interpulse interval sufficient for neural response.

A Charge Imbalance Module 706 is configured for calculating accumulated charge imbalance and charge imbalance polarity, step 503, which are used by the Pulse Generation Module 704 to generate the electrode stimulation signals. In specific embodiments, the Charge Imbalance Module 706 may be located in an implanted stimulation processor implanted under the skin of a patient user, or in an external signal processor attached to the skin of a patient user. And the Charge Imbalance Module 706 may be specifically configured for calculating the accumulated charge imbalance in terms of maximum comfortable level (MCL) for each electrode contact and/or the defined charge imbalance threshold value may be defined in terms of maximum comfortable level (MCL) for each electrode contact.

The details of generating the electrode stimulation signals are shown by the flowchart blocks in FIG. 6 where the first two steps specifically are, for each electrode contact after each stimulation pulse, the Charge Imbalance Module 706 calculates the accumulated charge imbalance, step 601 and the charge imbalance polarity, step 602. Then for each electrode contact, the Pulse Generation Module 704 generates the stimulation pulse sequence using a two-step decision process. The Pulse Generation Module 704 generates the next stimulation pulse with the same polarity as an immediately preceding stimulation pulse for that electrode contact only when the charge imbalance polarity has opposite polarity from the immediately preceding stimulation pulse for that electrode contact, step 603, and the accumulated charge imbalance exceeds the defined charge imbalance threshold value, step 605. Otherwise, each stimulation pulse has the opposite polarity as the immediately preceding stimulation pulse for that electrode contact. So if the charge imbalance polarity is not opposite the polarity of the preceding stimulation pulse in step 603, then the Pulse Generation Module 704 generates the next stimulation pulse in the sequence with opposite polarity from that of the preceding stimulation pulse, step 604. Or if the charge imbalance polarity is opposite from the polarity of the preceding stimulation pulse in step 603, but the accumulated charge imbalance is less than some a defined charge imbalance threshold value (e.g., 50% of MCL) in step 605, then the Pulse Generation Module 704 still generates the next stimulation pulse in the sequence with opposite polarity from that of the preceding stimulation pulse in step 604.

FIG. 10 shows an example of a stimulation pulse sequence on a single electrode contact according to an embodiment of the present invention. In this example, the defined charge imbalance threshold value is set to 50% MCL. Positive polarity stimulation pulses contribute to the accumulated charge imbalance with positive sign, while negative polarity stimulation pulses contribute with negative sign. In the example in FIG. 10, the stimulation pulse amplitudes also are given in terms of percentage relative to MCL. FIG. 10 shows amount of accumulated charge imbalance below each stimulation pulse in terms of percentage of MCL. The stimulation pulses may have a constant or variable pulse width, and the interpulse interval may be a fixed time duration or a variable time duration depending on the specific selected signal coding strategy.

The first stimulation pulse in FIG. 10 is applied with positive polarity and an amplitude of 100% MCL, followed by a stimulation pulse with opposite polarity at 70% MCL. The accumulated charge imbalance afterwards is 30% MCL (100−70). After applying two more stimulation pulses, the charge imbalance polarity is opposite from the polarity of the preceding stimulation pulse (the fourth pulse in the sequence) and the accumulated charge imbalance also has increased to 60% MCL (100−70+90−60), thus exceeding the 50% MCL that is the defined charge imbalance threshold value. Therefore the polarity of the fifth stimulation pulse does not switch, but remains the same negative polarity as the immediately preceding stimulation pulse to reduce the accumulate charge imbalance to −30% MCL. The sequence of stimulation pulses then resume with alternating polarity until the charge imbalance polarity again is opposite from the polarity of the preceding stimulation pulse and the accumulated charge imbalance also again exceeds the defined charge imbalance threshold value after the twelfth stimulation pulse (−70% MCL). Then the thirteenth stimulation pulse will remain at the same positive polarity as the preceding twelfth stimulation pulse, again reducing the accumulated charge imbalance (to zero). The same thing happens after the seventeenth stimulation pulse with the following eighteenth stimulation pulse (−60% MCL).

In the example shown in FIG. 10, the time sequence of stimulation pulses ends with a final charge balancing stimulation pulse having a polarity and amplitude that offsets the accumulated charge imbalance and charge imbalance polarity so that after the final charge balancing stimulation pulse the accumulated charge imbalance is zero.

The Pulse Generation Module 704 also will typically further adjust output the electrode stimulation signals based on a non-linear mapping that reflects patient-specific scaling from the fitting process, e.g., THR and MCL. Instead of applying a single output stimulation pulse for each selected timing pulse, the Pulse Generation Module 704 can use frequency specific pulse sequences for one or more selected electrode contacts. Such pulse sequences can vary in interpulse intervals and amplitude shape. Amplitude shapes can be based on templates, or the amplitudes can fall with a decay, e.g. with an exponential characteristic. In some embodiments, rather than generating a single output stimulation pulse for each selected timing pulse, the Pulse Generation Module 704 may excite an output pulse oscillator with the selected timing pulses. For example, such output pulse oscillators can be damped oscillators with electrode specific resonance frequencies; for example, the center frequencies assigned to each electrode contact. The oscillation then provides amplitudes for stimulation pulses which are applied on pulse sequences.

In some embodiments, the Pulse Generation Module 704 can be configured to apply the electrode stimulation signals via virtual channels (two simultaneous neighboring channels). So if first electrode contact E1 is assigned to a frequency band of 100 to 200 Hz and the second E2 to 200 to 300 Hz, then an instantaneous frequency of, for example, 200 Hz would lead to stimulation AMP1=(MCL1−THR1)/

2+THR1 and AMP2=(MCL2−THR2)/2+THR2. This would allow a fine spectral and temporal representation of the output stimulation pulses.

Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A signal processing system for a hearing implant system having an implanted electrode array with a plurality of electrode contacts configured for delivering electrode stimulation signals to adjacent auditory neural tissue, the system comprising:
   a band pass filter bank configured for processing an audio input signal to generate a plurality of band pass signals each representing an associated band of audio frequencies in the audio input signal;
   a stimulation signal processor configured for generating electrode stimulation signals for the electrode contacts based on the band pass signals, the electrode stimulation signals having an amplitude based on the envelope of their associated band pass filter, wherein for each electrode contact, the electrode stimulation signal is a sequence of monophasic stimulation pulses varying in polarity between positive polarity and negative polarity with successive pulses separated in time by an interpulse interval sufficient for neural response; and
   a charge imbalance module configured for calculating accumulated charge imbalance and charge imbalance polarity for each electrode contact after each stimulation pulse;
   wherein for each electrode contact:
   i. a stimulation pulse has the same polarity as an immediately preceding stimulation pulse for that electrode contact only when:
      (1) the charge imbalance polarity has opposite polarity from the immediately preceding stimulation pulse for that electrode contact, and
      (2) the accumulated charge imbalance exceeds a defined charge imbalance threshold value, and
   ii. otherwise, each stimulation pulse has the opposite polarity as the immediately preceding stimulation pulse for that electrode contact.

2. The signal processing system according to claim 1, wherein the charge imbalance module is configured for calculating the accumulated charge imbalance in terms of maximum comfortable level (MCL) for each electrode contact.

3. The signal processing system according to claim 1, wherein the defined charge imbalance threshold value is defined in terms of maximum comfortable level (MCL) for each electrode contact.

4. The signal processing system according to claim 1, wherein each sequence of monophasic stimulation pulses ends with a final charge balancing stimulation pulse having a polarity and amplitude offsetting the accumulated charge imbalance and charge imbalance polarity so that after the final charge balancing stimulation pulse the accumulated charge imbalance is zero.

5. The signal processing system according to claim 1, wherein the stimulation pulses have a constant pulse width.

6. The signal processing system according to claim 1, where the stimulation pulses have a variable pulse width.

7. The signal processing system according to claim 1, wherein the interpulse interval is a fixed time duration.

8. The signal processing system according to claim 1, wherein the interpulse interval is a variable time duration.

9. The signal processing system according to claim 1, wherein the charge imbalance module is located in an implanted stimulation processor configured for implanting under the skin of a patient user.

10. The signal processing system according to claim 1, wherein the charge imbalance module is located in an external signal processor configured for attaching to the skin of a patient user.

11. A computer based method implemented using at least one hardware implemented processor for generating electrode stimulation signals to electrode contacts in an implanted cochlear implant electrode array, the method comprising:
   using the at least one hardware implemented processor to perform the steps of:
   processing an audio input signal to generate a plurality of band pass signals, each band pass signal representing an associated range of audio frequencies;
   generating electrode stimulation signals for the electrode contacts based on the band pass signals, the electrode stimulation signals having an amplitude based on the envelope of their associated band pass filter, wherein for each electrode contact, the electrode stimulation signal is a sequence of monophasic stimulation pulses varying in polarity between positive polarity and negative polarity with successive pulses separated in time by an interpulse interval sufficient for neural response; and calculating accumulated charge imbalance and charge imbalance polarity for each electrode contact after each stimulation pulse;

wherein for each electrode contact:
- iii. a stimulation pulse has the same polarity as an immediately preceding stimulation pulse for that electrode contact only when:
  - (1) the charge imbalance polarity has opposite polarity from the immediately preceding stimulation pulse for that electrode contact, and
  - (2) the accumulated charge imbalance exceeds a defined charge imbalance threshold value, and
- iv. otherwise, each stimulation pulse has the opposite polarity as the immediately preceding stimulation pulse for that electrode contact.

12. The method according to claim 11, wherein the accumulated charge imbalance is calculated in terms of maximum comfortable level (MCL) for each electrode contact.

13. The method according to claim 11, wherein the defined charge imbalance threshold value is defined in terms of maximum comfortable level (MCL) for each electrode contact.

14. The method according to claim 11, wherein each sequence of monophasic stimulation pulses ends with a final charge balancing stimulation pulse having a polarity and amplitude offsetting the accumulated charge imbalance and charge imbalance polarity so that after the final charge balancing stimulation pulse the accumulated charge imbalance is zero.

15. The method according to claim 11, wherein the stimulation pulses have a constant pulse width.

16. The method according to claim 11, where the stimulation pulses have a variable pulse width.

17. The method according to claim 11, wherein the interpulse interval is a fixed time duration.

18. The method according to claim 11, wherein the interpulse interval is a variable time duration.

19. The method according to claim 11, wherein the accumulated charge imbalance and charge imbalance polarity are calculated by an implanted stimulation processor implanted under the skin of a patient user.

20. The method according to claim 11, wherein the accumulated charge imbalance and charge imbalance polarity are calculated by an external signal processor attached to the skin of a patient user.

\* \* \* \* \*